United States Patent
Wyart et al.

(10) Patent No.: US 10,533,017 B2
(45) Date of Patent: Jan. 14, 2020

(54) METHOD FOR PRODUCING DIANHYDROHEXITOL WITH A STEP OF DISTILLATION ON A THIN-FILM EVAPORATOR

(71) Applicant: ROQUETTE FRERES, Lestrem (FR)

(72) Inventors: Hervé Wyart, Cuinchy (FR); Mathias Ibert, La Chapelle d'Armentières (FR)

(73) Assignee: ROQUETTE FRERES, Lestrem (FR)

( * ) Notice: Subject to any disclaimer, the term of this patent is extended or adjusted under 35 U.S.C. 154(b) by 0 days.

(21) Appl. No.: 16/085,903

(22) PCT Filed: Mar. 16, 2017

(86) PCT No.: PCT/FR2017/050608
§ 371 (c)(1),
(2) Date: Sep. 17, 2018

(87) PCT Pub. No.: WO2017/158303
PCT Pub. Date: Sep. 21, 2017

(65) Prior Publication Data
US 2019/0092782 A1 Mar. 28, 2019

(30) Foreign Application Priority Data
Mar. 16, 2016 (FR) ...................... 16 52236

(51) Int. Cl.
C07D 493/04 (2006.01)
B01D 1/22 (2006.01)
B01D 3/14 (2006.01)

(52) U.S. Cl.
CPC .............. C07D 493/04 (2013.01); *B01D 1/22* (2013.01); *B01D 3/14* (2013.01)

(58) Field of Classification Search
CPC ........... C07D 493/04; B01D 1/22; B01D 3/14
USPC ...................................................... 549/464
See application file for complete search history.

(56) References Cited

U.S. PATENT DOCUMENTS

| | | | |
|---|---|---|---|
| 3,160,641 A | 12/1964 | Hartmann | |
| 4,408,061 A | 10/1983 | Salzburg et al. | |
| 4,861,513 A | 8/1989 | Lueders et al. | |
| 2004/0152907 A1* | 8/2004 | Moore | C07D 493/04 549/476 |
| 2007/0213544 A1 | 9/2007 | Sanborn | |
| 2015/0126599 A1 | 5/2015 | Sanborn et al. | |

FOREIGN PATENT DOCUMENTS

| | | |
|---|---|---|
| CA | 1 178 288 A | 11/1984 |
| EP | 2 848 603 A1 | 3/2015 |
| GB | 613 444 A | 11/1948 |
| KR | 20140048436 A | 4/2014 |
| WO | 89/00162 A1 | 1/1989 |
| WO | 03/089445 A2 | 10/2003 |
| WO | 2005/047228 A1 | 5/2005 |
| WO | 2013/169029 A1 | 11/2013 |
| WO | 2014/73843 A1 | 5/2014 |
| WO | 2014/129834 A1 | 8/2014 |
| WO | 2014/177815 A1 | 11/2014 |

OTHER PUBLICATIONS

Wiggins, L. F., "Interconversion of Dianhydro Hexitols and of Saccharic Acids", Nature, No. 4170, Oct. 1, 1949, pp. 573-574.
May 18, 2017 Search Report issued in International Patent Application No. PCT/FR2017/050608.

* cited by examiner

Primary Examiner — Taylor V Oh
(74) Attorney, Agent, or Firm — Oliff PLC

(57) ABSTRACT

A method for producing 1,4:3,6-dianhydrohexitols, including the steps of: a) supplying at least one hexitol, b) dehydrating the hexitol, and c) distillating the dehydration product produced in step b), wherein: the hexitol is supplied in the form of an aqueous solution in step a); and the distillation is carried out by means of a thin-film evaporator in step c).

11 Claims, No Drawings

METHOD FOR PRODUCING DIANHYDROHEXITOL WITH A STEP OF DISTILLATION ON A THIN-FILM EVAPORATOR

The present invention relates to a process for manufacturing 1,4:3,6-dianhydrohexitols, by providing an aqueous solution of at least one hydrogenated sugar, internal dehydration thereof, and distillation of the product obtained by means of a thin-film evaporator. Throughout the present patent application, the terms "thin-layer", "thin-film" and "scraped-film" evaporator will be used equivalently.

This process differs from the prior art methods which resort to distillation as a batchwise unitary purification step, which lead to lower yields and to more colored products. Products that are esthetically more acceptable and chemically more stable are thus obtained according to the invention. In addition, batchwise distillation techniques often recommend the use of products for facilitating said distillation; said auxiliaries prove to be hazardous to man or harmful to the environment.

The process according to the invention also differs from the prior art in the sense that it uses as starting material an aqueous solution rather than a powder: pulverulent products give rise to handling problems, but are also a source of hazard; they must moreover be melted, which has a major economic impact on the process under consideration.

The economic upgrading of renewable biological resources has become a major ecological and economic imperative, in the face of the depletion and of the increase in costs of fossil materials such as petroleum. The development of 1,4:3,6-dianhydrohexitols falls within this context.

These products, also referred to as isohexides, are obtained by internal dehydration of hydrogenated $C_6$ sugars (hexitols) such as sorbitol, mannitol and iditol. In the present patent application, the term "dianhydrohexitols" encompasses isosorbide (1,4:3,6-dianhydrosorbitol), isomannide (1,4:3,6-dianhydromannitol) and isoidide (1,4:3,6-dianhydroiditol) of the following formulae, and also mixtures of these products:

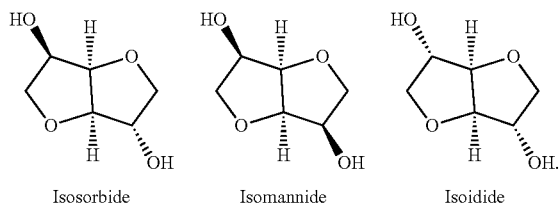

Isosorbide     Isomannide     Isoidide

The Applicant indicates that these products may also be obtained by deamination, according to the method described in the document "Interconversion of DianhydroHexitols and of Saccharic Acids" (Nature, Oct. 1, 1949, vol. 464, pages 573-574), such a method remaining marginal, to say the least, in the industrial sector.

There is at the present time great potential for the industrial development of isohexides, especially in the pharmaceutical sector, in the manufacture of chemical synthetic intermediates and in the plastics sector.

By way of example, patent GB 613 444 describes the production, by dehydration in water/solvent medium, of an isosorbide composition which is then subjected to a distillation treatment and then recrystallization from an alcohol/ether mixture.

A purification treatment combining distillation and recrystallization from a lower aliphatic alcohol (ethanol or methanol) is also recommended in patent WO 00/14081. Said document indicates that, in the case where distillation is the only purification step envisaged, it is advantageous to use sodium borohydride.

Other authors have also recommended that the distillation step be performed in the presence of a boron compound such as boric acid or with an anionic resin charged with borate ions, as described in patent U.S. Pat. No. 3,160,641.

U.S. Pat. No. 4,408,061 and EP 0 323 994 envisage the use of particular dehydration catalysts (a gaseous hydrogen halide and liquid hydrogen fluoride, respectively), advantageously combined with carboxylic acids as co-catalysts, followed by distillation of the crude isosorbide or isomannide compositions thus obtained.

It results from the foregoing that the production of isohexide-based compositions generally imposes the use, at least at one given moment, of means that are expensive to say the least, such as hydrogen halides combined with anhydrization catalysts and cocatalyst, or potentially hazardous to man and the environment, and in any case whose use is strictly regulated, such as organic solvents. This is all the more detrimental since the abovementioned techniques resort to distillation as the final purification step, distillation being an operation that is very widely known to those skilled in the art, commercially available, readily usable and perfectly suited to industrial use.

Subsequent solutions have been proposed, for the purpose of providing a process for obtaining compositions containing isohexides, involving a distillation step. In this respect, patent applications WO 2005/047228, WO 2013/169029, WO 2014/073843, WO 2014/129834 and KR 20140048436 are known. All these documents describe processes for manufacturing isosorbide, in which the final purification step is performed by distillation, using a thin-film evaporator.

This type of device is composed of a cylindrical part heated by a jacket, an upper part which serves for separating out the vapors and a rotor rotating at high speed. The product to be treated, introduced into the upper part of the cylindrical part, is also spread over the heating surface by means of a distributing ring. It is taken up by the rotor vanes and instantaneously spread over the entire wall in the form of a highly turbulent film. The product descends toward the base of the apparatus following a helical movement along the inner wall, during which the evaporation of the volatile products takes place. The vapors that are formed rise counter-currentwise toward the top of the apparatus and pass through the separator. The droplets and the foams entrained are retained and fall in the evaporation zone. The vapors thus released from the liquid particles pass into a condenser, into a column or any other following process stage.

The five abovementioned patent applications, while involving the thin-film evaporation technology, also have two other common characteristics: the initial product is a sorbitol in powder form, and this powder is then heated to obtain a melt. The pulverulent nature of the starting sorbitol poses numerous problems: it is well known that powders have risks of explosion, but are also difficult to store and transport because of caking problems. Furthermore, it is necessary to expend a large amount of energy in order to transform said powder into a melt, which is at variance with an economical process.

Finally, patent application WO 2009/126852 is known. It describes a process which consists in dehydrating sorbitol under vacuum in the presence of an acid catalyst. According to a particular variant, said sorbitol is present in the form of an aqueous solution with a solids content of between 40% and 95% of its total weight. Example 7 thereof describes a synthesis of isosorbide starting with an aqueous solution of sorbitol containing 93% by dry weight of product. The synthesis is followed by a standard batchwise distillation. Nevertheless, the Applicant noted that, in such a process, the final product obtained is characterized by a dark yellow color. Now, it is well known that these coloration phenomena reflect the presence of impurities of diverse nature which may be detrimental to the stability of the product, but also to its use in the final application.

Consequently, there is at the present time no method for manufacturing isohexide compositions advantageously involving a simple continuous distillation step for the purpose of purifying the final product, which is free of compounds that are harmful to man and the environment, which does not have the drawback of using a product in powder form that needs to be melted, and which leads to final products of satisfactory color.

After conducting numerous research studies, the Applicant Company has succeeded in developing such a method. This method consists of a process for manufacturing 1,4:3,6-dianhydrohexitols, comprising the steps of:
  a) providing at least one hexitol,
  b) dehydrating said hexitol,
  c) distilling the dehydration product obtained on conclusion of step b), characterized in that:
  the hexitol is provided in the form of an aqueous solution in step a),
  the distillation is performed using a thin-film evaporator in step c).

The first step of the process that is the subject of the present invention consists in providing at least one hexitol, said hexitol being provided in the form of an aqueous solution.

This step is performed continuously.

Preferably, this aqueous solution has a dry weight content of hexitol of greater than 95%, preferentially greater than 96%, very preferentially greater than or equal to 97% of its total weight, and less than 99% of its total weight.

This aqueous solution is preferentially obtained by removing the water from an initial aqueous solution containing at least one hexitol, and the dry weight content of said hexitol is between 40% and 80% of its total weight. The removal of the water is performed via any means well known to those skilled in the art, especially by heating, in particular by vacuum distillation. The initial aqueous solution is, for example, a product sold by the Applicant under the name Neosorb.

The aqueous solution containing at least one hexitol is also characterized in that the hexitol is chosen from sorbitol, mannitol and iditol, and mixtures thereof, and is preferentially sorbitol.

The second step of the process according to the invention consists in performing, on the solution containing at least one hexitol and provided during the first step, dehydration of said hexitol so as to obtain a 1,4:3,6-dianhydrohexitol.

This step is in no way limiting for the process that is the subject of the present patent application. It may be performed according to any of the processes that are well known to those skilled in the art. In this respect, mention may be made of patent CA 1 178 288, which recalls on page 14, lines 3-8 thereof that it is recommended to perform the dehydration reaction per se under an atmosphere of an inert gas to avoid oxidation reactions, especially when relatively high reaction temperatures and long reaction times are envisaged. One variant according to the present invention thus consists in performing this dehydration step under an atmosphere of an inert gas.

U.S. Pat. No. 4,861,513 describes a sorbitol dehydration reaction performed in the simultaneous presence of an inert gas (nitrogen) and of a reducing agent (sodium hypophosphite) for the purpose of preparing mixtures of particular polyols, which have a low content (10 to 26%) of dianhydrosorbitol. The abovementioned patent GB 613 444, for its part, describes the production, by dehydration in water/solvent medium, of an isosorbide composition which is then subjected to a distillation treatment and then recrystallization from an alcohol/ether mixture.

Preferably, the conditions for performing this dehydration step are the following: the solution containing the hexitol obtained during the first step is introduced into a reactor. Simultaneously, before or after the introduction of the hexitol solution, the dehydration catalyst is introduced into the reactor. This catalyst may be of any type, provided that it allows dehydration of the hexitol in the subsequent step. This catalyst may be a heterogeneous catalyst or a homogeneous catalyst. It may be an acid catalyst, in particular a strong acid catalyst, or ion-exchange resins, in particular acidic cation-exchange resins, or acidic zeolite-type catalysts. The acid catalyst may in particular be sulfuric acid, hydrochloric acid, para-toluenesulfonic acid, phosphoric acid or methanesulfonic acid. Sulfuric acid is a catalyst that is particularly preferred for the production of the composition according to the invention.

The acidic cation-exchange resin may be a sulfonated polystyrene resin such as the AG50W-X12 resin from Bio-Rad. The acidic zeolite may be a beta-zeolite.

The dehydration catalyst is introduced in amounts which allow the dehydration step to be performed. In particular, when sulfuric acid is used, it is preferred to use amounts of less than 2% by mass relative to the total mass of hexitol, preferably less than 1.5%, most preferentially less than 1.2%.

The dehydration step can be carried out under vacuum, under a stream of an inert gas, for example nitrogen, or else under pressure in an autoclave, these three methods making it possible to facilitate the elimination of the water and thus to shift the reaction equilibrium.

In order to carry out the dehydration step, it is necessary to provide the reactor with heat. This required amount of heat depends mainly on the nature and amount of catalyst used and, to a lesser extent, on the pressure conditions in the reactor during the dehydration step. To provide the required heat, the temperature inside the reactor and in which the dehydration reaction is performed may range from 110° C. to 400° C. depending on the catalyst used. For example, when 1% by mass of sulfuric acid is used, relative to the mass of hexitol introduced, a temperature greater than or equal to 135° C., advantageously greater than or equal to 150° C., is preferably used. Advantageously, the temperature remains below 300° C.

At the end of the dehydration step, when a homogeneous acid catalyst is used, a step of neutralizing the catalyst is preferably carried out.

Finally, the third step of the process that is the subject of the present invention consists in distilling the product obtained on conclusion of the preceding dehydration step, i.e. 1,4:3,6-dianhydrohexitol, the distillation being performed with a thin-film evaporator. This step is performed under vacuum and temperature conditions which allow the isohexide to be isolated from the rest of the constituents of the product.

The preferred conditions for performing this step are the following. The product obtained on conclusion of the preceding dehydration step is introduced continuously by means of a pump into the upper part of the cylindrical body of a thin-film evaporator. It is then spread over the heated walls of the cylindrical body by the rotor vanes. The temperature of the jacket is maintained between 160° C. and 230° C., preferentially between 170° C. and 220° C. The vacuum applied during the distillation is less than 50 mbar, preferentially less than 20 mbar, very preferentially less than 10 mbar.

The Gardner color of the 1,4:3,6-dianhydrohexitol obtained after distillation, as measured on the melted product in a cell with an optical path length of 1 cm using a Lovibond PFXi-195/1 colorimeter is less than or equal to 4, in particular less than or equal to 3, more particularly less than or equal to 2.5, more particularly less than or equal to 2.1.

EXAMPLES

Example 1 According to the Invention 1 kg of a sorbitol solution with a solids content of 70% (i.e. 700 g dry) sold by the Applicant under the name Neosorb® 70/02 is introduced into a 1 liter Schott brand glass reactor, equipped with a jacket fed with an oil-circulation thermostatic bath, a stirring paddle, a thermometer, a distillation head combined with a condenser and a distillation receiver. The whole assembly is then connected to a vacuum pump equipped with a vacuum gauge. Stirring is switched on at 650 rpm. The sorbitol solution is then heated under vacuum (120° C.-100 mbar) so as to distil off the water present in the solution. After distillation of 279 g of water, 721 g of a sorbitol solution containing 97% solids are obtained. 7 g of concentrated sulfuric acid are added and the mixture obtained is then heated under vacuum (pressure of about 100 mbar) at 150° C. for 3 hours so as to perform the sorbitol dehydration reaction.

The reaction crude is then cooled to 100° C. and then neutralized with 11.4 g of a 50% sodium hydroxide solution. 575 g of a neutralized isohexide composition containing 71.5%, i.e. 411 g, of isosorbide are obtained. The composition obtained is then introduced over 2 hours by means of a gear pump into a VDL 70-4 glass scraped-film evaporator with an evaporation surface area of 0.05 m², the jacket of which is heated at 200° C. under a vacuum of 5 mbar. 395 g of distilled isosorbide are obtained, which corresponds to a distillation yield of 96.1%. The Gardner color of the isosorbide obtained after distillation is measured on the melted product in a cell with an optical path length of 1 cm, using a Lovibond PFXi-195/1 colorimeter. A color value of 2.1 Gardner is obtained.

Example 2

1 kg of a sorbitol solution with a solids content of 70% (i.e. 700 g dry) sold by the Applicant under the name Neosorb® 70/02 is introduced into a 1 liter Schott brand glass reactor, equipped with a jacket fed with an oil-circulation thermostatic bath, a stirring paddle, a thermometer, a distillation head combined with a condenser and a distillation receiver. The whole assembly is then connected to a vacuum pump equipped with a vacuum gauge. Stirring is switched on at 650 rpm. The sorbitol solution is then heated under vacuum (120° C.-100 mbar) so as to distil off the water present in the solution. After distillation of 279 g of water, 721 g of a sorbitol solution containing 97% solids are obtained. 7 g of concentrated sulfuric acid are added and the mixture obtained is then heated under vacuum (pressure of about 100 mbar) at 150° C. for 3 hours so as to perform the sorbitol dehydration reaction.

The reaction crude is then cooled to 100° C. and then neutralized with 11.4 g of a 50% sodium hydroxide solution. 575 g of a neutralized isohexide composition containing 71.5%, i.e. 411 g, of isosorbide are obtained. The composition obtained is left in the reactor, bringing the jacket temperature to 200° C., and a vacuum of 5 mbar is applied to perform the distillation. Under these conditions, 380 g of distilled isosorbide are obtained, which corresponds to a distillation yield of 92.5%. The color of the isosorbide obtained after distillation is 4.8 Gardner.

Example 3 According to the Invention 1 kg of a sorbitol solution with a solids content of 70% (i.e. 700 g dry) sold by the Applicant under the name Neosorb® 70/02 is introduced into a 1 liter Schott brand glass reactor, equipped with a jacket fed with an oil-circulation thermostatic bath, a paddle stirrer, a thermometer, a distillation head combined with a condenser and a distillation receiver. The whole assembly is then connected to a vacuum pump equipped with a vacuum gauge. Stirring is switched on at 650 rpm. The sorbitol solution is then heated under vacuum (125° C.-100 mbar) so as to distil off the water present in the solution. After distillation of 285 g of water, 715 g of a sorbitol solution containing 97.9% solids are obtained. 10.5 g of concentrated methanesulfonic acid are added and the mixture obtained is then heated under vacuum (pressure of about 100 mbar) at 150° C. for 3 hours so as to perform the sorbitol dehydration reaction.

The reaction crude is then cooled to 100° C. and then neutralized with 8.8 g of a 50% sodium hydroxide solution. 580 g of a neutralized isohexide composition containing 70.8%, i.e. 410 g, of isosorbide are obtained. The composition obtained is then introduced over 2 hours by means of a gear pump into a VDL 70-4 glass scraped-film evaporator with an evaporation surface area of 0.05 m², the jacket of which is heated at 180° C. under a vacuum of 15 mbar. 372 g of distilled isosorbide are obtained, which corresponds to a distillation yield of 90.7%. The Gardner color of the isosorbide obtained after distillation is measured on the melted product in a cell with an optical path length of 1 cm, using a Lovibond PFXi-195/1 colorimeter. A color value of 1.6 Gardner is obtained.

Example 4 According to the Invention 1 kg of a sorbitol solution with a solids content of 70% (i.e. 700 g dry) sold by the Applicant under the name Neosorb® 70/02 is introduced into a 1 liter Schott brand glass reactor, equipped with a jacket fed with an oil-circulation thermostatic bath, a stirring paddle, a thermometer, a distillation head combined with a condenser and a distillation receiver. The whole assembly is then connected to a vacuum pump equipped with a vacuum gauge. Stirring is switched on at 650 rpm. The sorbitol solution is then heated under vacuum (125° C.-100 mbar) so as to distil off the water present in the solution. After distillation of 285 g of water, 715 g of a sorbitol solution containing 97.9% solids are obtained. 70 g of dry Amberlyst 36 macroporous resin are added and the mixture obtained is then heated under vacuum (pressure of about 100 mbar) at 150° C. for 3 hours so as to perform the sorbitol dehydration reaction.

The crude reaction product is then cooled to about 100° C. and then filtered to separate the reaction medium from the resin. 568 g of an isohexide composition containing 72.0%, i.e.

409 g, of isosorbide are obtained. The composition obtained is then introduced over 2 hours by means of a gear pump into a VDL 70-4 glass scraped-film evaporator with an evaporation surface area of 0.05 m², the jacket of which is heated at 190° C. under a vacuum of 10 mbar. 384 g of distilled isosorbide are obtained, which corresponds to a distillation yield of 93.8%. The Gardner color of the isosorbide obtained after distillation is measured on the melted product in a cell with an optical path length of 1 cm, using a Lovibond PFXi-195/1 colorimeter. A color value of 1.9 Gardner is obtained.

These four tests thus clearly illustrate the possibility of obtaining isosorbide via a process according to the present invention.

The use of powder as starting material is avoided, which frees the user from the constraints of handling pulverulent products and eliminates the explosion risks associated with the use of this type of product.

Finally, the color of the final product is greatly improved, when compared with batchwise techniques.

The invention claimed is:

1. A process for manufacturing 1,4:3,6-dianhydrohexitols, comprising the following steps in order:
    a) providing at least one hexitol,
    b) dehydrating said hexitol,
    c) distilling the dehydration product obtained on conclusion of step b), wherein:
    the hexitol is provided in the form of an aqueous solution having a dry weight content of hexitol of greater than 95% of its total weight in step a),
    the distillation is performed using a thin-film evaporator in step c).

2. The process as claimed in claim 1, wherein the aqueous solution has a dry weight content of hexitol of greater than 96% and less than 99% of its total weight.

3. The process as claimed in claim 1, wherein the aqueous solution is obtained by removing the water from an initial aqueous solution containing at least one hexitol, and of which the dry weight content of said hexitol is between 40% and 80% of its total weight.

4. The process as claimed in claim 1, wherein, for the aqueous solution containing at least one hexitol, said hexitol is chosen from sorbitol, mannitol and iditol, and mixtures thereof.

5. The process as claimed in claim 1, wherein the dehydration step is performed in the presence of a dehydration catalyst.

6. The process as claimed in claim 5, wherein the catalyst an ion-exchange resin catalyst, an acidic cation-exchange resin catalyst, or an acidic zeolite catalyst.

7. The process as claimed in claim 5, wherein the catalyst is an acid catalyst chosen from sulfuric acid, hydrochloric acid, para-toluenesulfonic acid, phosphoric acid and methanesulfonic acid.

8. The process as claimed in claim 1, wherein the dehydration step is performed under vacuum, under a stream of an inert gas, or under pressure in an autoclave.

9. The process as claimed in claim 1, wherein the dehydration step is performed at a temperature from 110° C. to 400° C.

10. The process as claimed in claim 1, wherein the distillation step is performed at a temperature of between 160° C. and 230° C.

11. The process as claimed in claim 1, wherein the distillation step is performed under a vacuum of less than 50 mbar.

* * * * *